United States Patent [19]

Slongo et al.

[11] Patent Number: 4,537,923

[45] Date of Patent: Aug. 27, 1985

[54] POLYALKYLPIPERIDINESULFONIC ACID ESTERS

[75] Inventors: Mario Slongo, Tafers; Friedrich Karrer, Zofingen, both of Switzerland

[73] Assignee: Ciba Geigy Corporation, Ardsley, N.Y.

[21] Appl. No.: 503,436

[22] Filed: Jun. 13, 1983

[30] Foreign Application Priority Data

Jun. 17, 1982 [CH] Switzerland .................. 3743/82

[51] Int. Cl.³ .................. C08K 5/34; C08G 63/04
[52] U.S. Cl. .................. 524/100; 524/102; 524/103; 525/157; 525/158; 525/167; 525/443; 525/444; 528/294; 528/314
[58] Field of Search .............. 525/157, 158, 167, 443, 525/444; 524/100, 102, 103; 528/294, 314

[56] References Cited

U.S. PATENT DOCUMENTS

| 2,227,708 | 1/1941 | Cordier | 524/14 |
|---|---|---|---|
| 2,839,562 | 6/1958 | Wegler et al. | 260/456 A |
| 3,474,054 | 10/1969 | White | 525/443 |
| 3,979,478 | 9/1976 | Gallacher | 525/443 |
| 4,083,830 | 4/1978 | Gallacher | 525/443 |
| 4,192,826 | 3/1980 | Beresniewicz et al. | 525/425 |
| 4,197,236 | 4/1980 | Rosenberger et al. | 524/99 |
| 4,291,137 | 9/1981 | Nakate et al. | 525/162 |
| 4,344,876 | 8/1982 | Berner | 106/176 |
| 4,426,471 | 1/1984 | Berner | 525/443 |
| 4,429,077 | 1/1984 | Karrer et al. | 525/157 |
| 4,482,698 | 11/1984 | Reesink | 525/157 |

FOREIGN PATENT DOCUMENTS

| 55216 | 6/1982 | European Pat. Off. | |
| 2345114 | 3/1975 | Fed. Rep. of Germany | 549/555 |

Primary Examiner—John Kight
Assistant Examiner—Kriellion Morgan
Attorney, Agent, or Firm—Harry Falber

[57] ABSTRACT

Polyalkylpiperidinesulfonic acid esters of the formulae I and II $$B-X-O-SO_2-A)_m \qquad (I)$$

$$(B'-X-O-SO_2)_2A' \qquad (II),$$

in which A, A', B, B', X and m are as defined in claim 1, the polyalkylpiperidine group being present in each of the substituents B and B'. These esters are suitable for use as curing catalysts for acid-curable resins and act therein, at the same time, as light stabilizers.

9 Claims, No Drawings

POLYALKYLPIPERIDINESULFONIC ACID ESTERS

The present invention relates to polyalkylpiperidinesulfonic acid esters and to their use as curing catalysts and light stabilizers for systems of finishes based on acid-curable resins.

Acid-curable resins are especially used as binders for finishes, printing inks and paints when high stoving temperatures are to be avoided. Acid-curable resins can be amino resins, including etherified, esterified or otherwise modified melamine resins, urea-formaldehyde resins, phenol-formaldehyde resins and mixtures of such resins with alkyd, polyester or acrylic resins. Other acid-curable resins are methylol compounds, methylol ethers of polycarboxylic acid imides, for example derivatives of polyacrylic or methacrylic acid, urethane alkyds and resins containing carboxylic acid esters of N-methylolimides. The acid curing catalysts used are principally organic acids, including, for example, sulfonic acids, especially p-toluenesulfonic acid. Since these acids cause a slow curing even at room temperature, they are only added to the resin shortly before the application of the latter, which is associated with the known problems of maintaining specific pot lives. The use of blocked curing catalysts, from which the acid is set free at elevated temperature has, therefore, already been suggested as a means of making one-component systems possible. Examples of these are amine salts of aromatic sulfonic acids, such as the pyridine salts suggested in U.S. Pat. No. 3,474,054. These and other salts have the disadvantage that they cause slow curing even during storage. In addition, odour problems are caused thereby.

In order to improve the stability on storage, it has further been suggested in German Offenlegungsschriften Nos. 2,345,114, 2,731,528 and 2,936,048 to use a reaction product formed from epoxide-containing compounds with organic sulfonic acids as a curing catalyst.

Novel polyalkylpiperidinesulfonic acid esters which can be employed at the same time as curing catalysts and as light stabilisers, and in which the abovementioned disadvantages do not occur, have now been found. Surprisingly, these esters decompose at the desired curing temperature with the formation of the sulfonic acid required for curing and of the polyalkylpiperidine derivative which remains in the finish as a light stabilizer.

Accordingly, the invention relates to compounds of the formula I and II $$B\text{-}(X\text{---}O\text{---}SO_2\text{---}A)_m \quad (I)$$

$$(B'\text{---}X\text{---}O\text{---}SO_2)_{\overline{2}}A' \quad (II)$$

in which m is a number 1 to 3, X is a direct bond or a group of the formula III

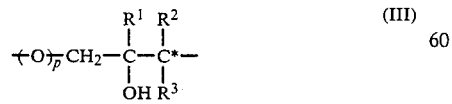

which is attached via C* to the oxygen of the sulfo group, p being zero if the group of the formula III is attached to a nitrogen atom of B or B', and p otherwise being the number 1, and $R^1$, $R^2$ and $R^3$ independently of one another being hydrogen or methyl, A is $C_1$–$C_{20}$-alkyl, $C_1$–$C_4$-alkoxy, $C_2$–$C_{12}$-alkenyl, $C_7$–$C_{12}$-aralkyl, $C_6$–$C_{10}$-aryl, $C_7$–$C_{30}$-alkaryl, $C_5$–$C_8$-cycloalkyl, trifluoromethyl or camphoryl, each of which is unsubstituted or substituted by hydroxyl, a group —N($R^4$)($R^5$) or —C(CH$_3$)$_2$—CH$_2$—N($R^6$)—C(O)—C($R^7$)=CH$_2$, in which $R^4$, $R^5$ and $R^6$ are hydrogen or $C_1$–$C_{12}$-alkyl and $R^7$ is hydrogen or methyl, or a group of the formula

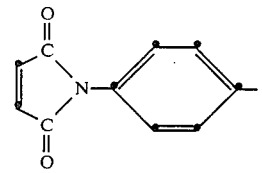

or of the formula

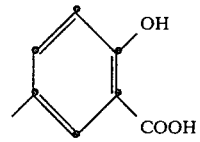

A' is $C_2$–$C_{20}$-alkylene, $C_6$–$C_{12}$-arylene or $C_7$–$C_{28}$-alkylarylene, and B, provided that m=1, and B' are a group of the formulae IV to X

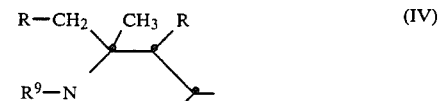

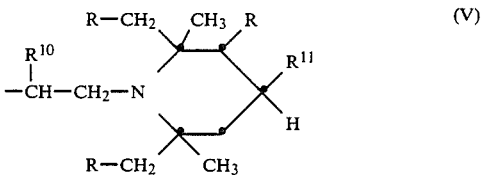

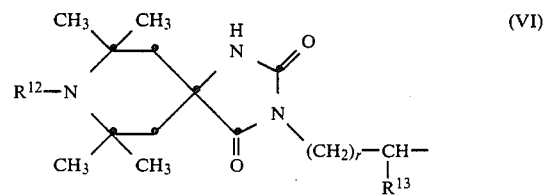

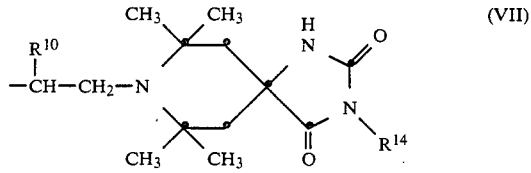

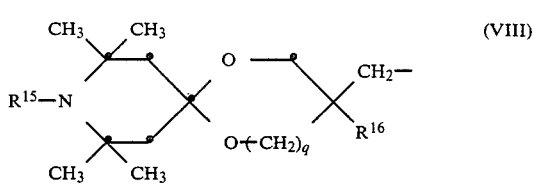

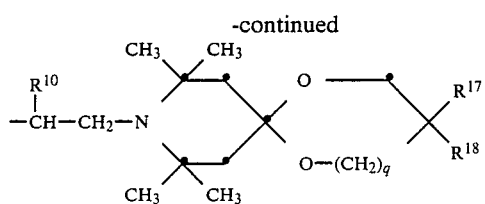  (IX)
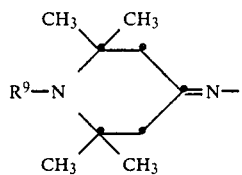  (X)
in addition, B, provided that m=1, and B′, provided that X is a group of the formula III, can also be a group of the formulae XI to XVI
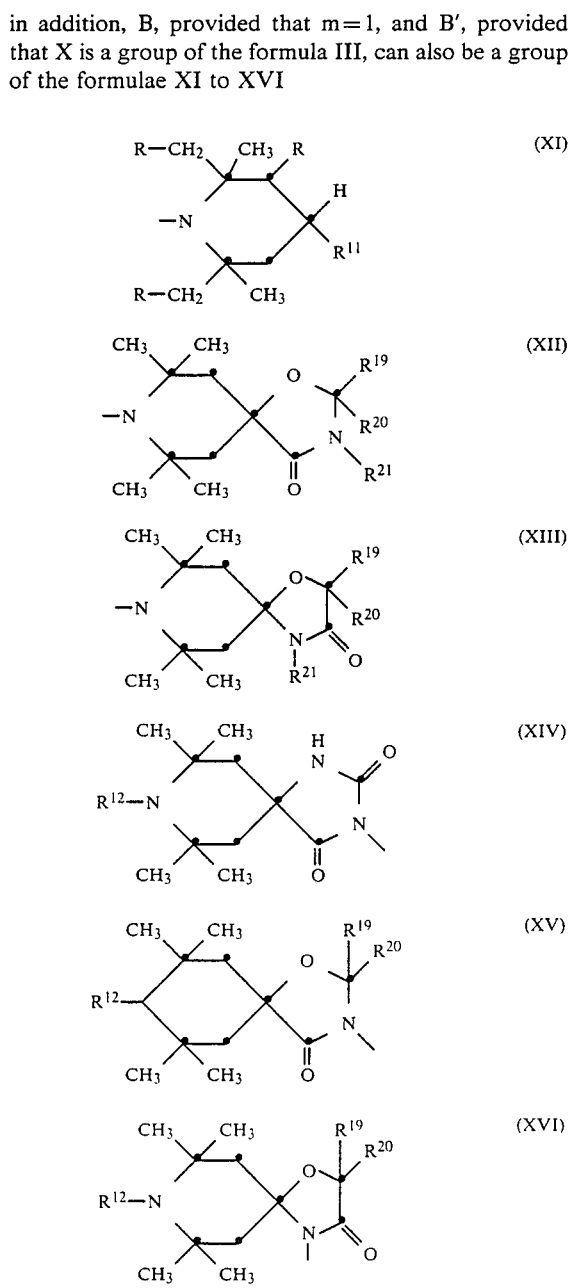
if m=2, B is a group of the formulae XVII to XX
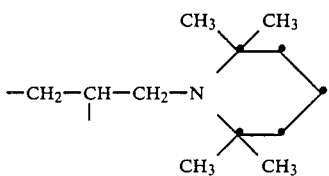  (XVII)
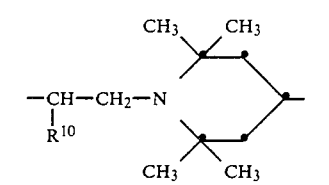  (XVIII)
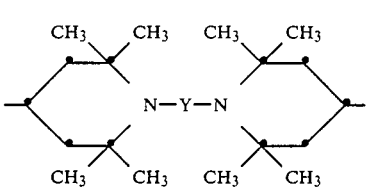  (XIX)
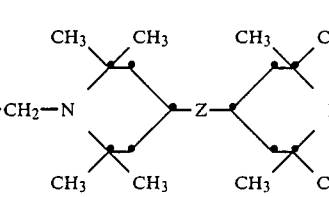  (XX)
In addition, if m=2 and if X is a group of the formula III, B can also be a group of the formulae XXI to XXV
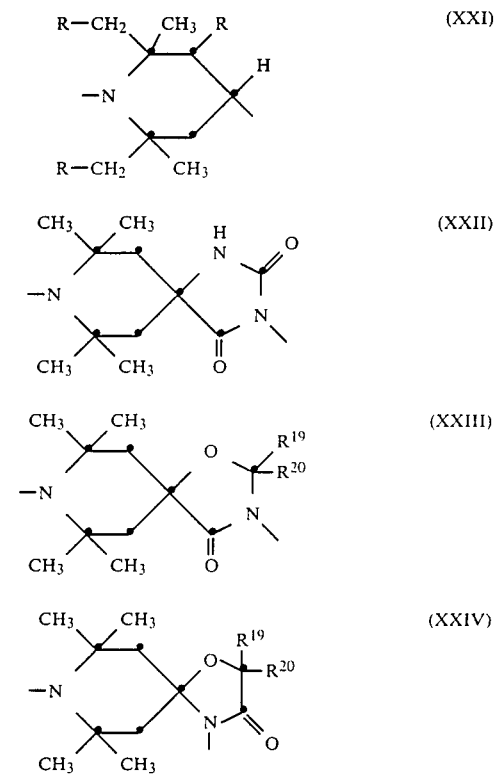

continued

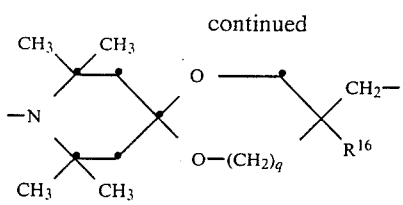
(XXV)

and, if m=3, B is a group of the formula XXVI

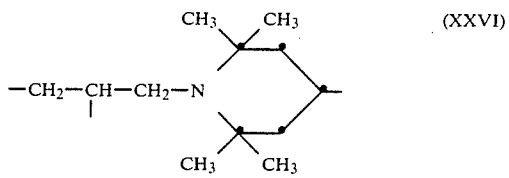
(XXVI)

and, in the formulae IV to XXV, R is hydrogen or methyl, $R^9$ is hydrogen, $C_1$–$C_{20}$-alkyl, $C_3$–$C_5$-alkenyl, $C_3$–$C_5$-alkynyl, $C_7$–$C_{12}$-aralkyl, $C_1$–$C_{18}$-acyl, $C_3$–$C_{10}$-alkoxycarbonylalkyl, $C_2$–$C_4$-hydroxyalkyl, cyanomethyl, oxyl, a group of the formula —$CH_2$—$CH(OH)$—$CH_2$—$OR^{27}$ or a group of the formula —C(O)—$N(R^{22})(R^{23})$, $R^{10}$ is hydrogen, $C_1$–$C_4$-alkyl, $C_1$–$C_4$-alkoxy, phenyl, phenoxy which is unsubstituted or substituted in the phenyl nucleus by $C_1$–$C_4$-alkyl, or phenoxymethyl, $R^{11}$ is hydrogen, hydroxyl, $C_1$–$C_{12}$-alkoxy, $C_3$–$C_5$-alkenyloxy, $C_1$–$C_{12}$-acyloxy, $C_1$–$C_{12}$-acylamino, $C_2$–$C_{14}$-alkoxycarbonyl or a group of the formula

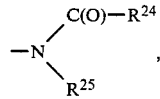

—C(O)—$N(R^{24})(R^{25})$, —OC(O)—$N(R^{24})(R^{25})$, or —$CH_2$—$COOR^{24}$, $R^{12}$ is hydrogen, $C_1$–$C_{12}$-alkyl, $C_3$–$C_5$-alkenyl, $C_3$–$C_5$-alkynyl, $C_7$–$C_{12}$-aralkyl, $C_1$–$C_{18}$-acyl, cyanomethyl or $C_2$–$C_4$-hydroxyalkyl, $R^{13}$ is hydrogen or $C_1$–$C_4$-alkyl, $R^{14}$ is hydrogen, $C_1$–$C_{20}$-alkyl, $C_3$–$C_5$-alkenyl, $C_3$–$C_5$-alkynyl, $C_7$–$C_{12}$-aralkyl or $C_6$–$C_8$-cycloalkyl, $R^{15}$ is hydrogen, $C_1$–$C_{12}$-alkyl, $C_3$–$C_5$-alkenyl, $C_7$–$C_{12}$-aralkyl, $C_1$–$C_{18}$-acyl, cyanomethyl or $C_2$–$C_4$-hydroxyalkyl, $R^{16}$ is hydrogen, methyl or ethyl, $R^{17}$ and $R^{18}$ independently of one another are hydrogen or $C_1$–$C_6$-alkyl or $R^{17}$ and $R^{18}$ together are one of the groups of the formulae

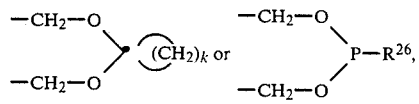

$R^{19}$ and $R^{20}$ independently of one another are hydrogen, $C_1$–$C_{12}$-alkyl, phenyl which is unsubstituted or substituted by $C_1$–$C_4$-alkyl, $C_5$–$C_8$-cycloalkyl or $C_7$–$C_{12}$-aralkyl or $R^{19}$ and $R^{20}$ together are $C_4$–$C_{11}$-alkylene, $R^{21}$ is hydrogen, $C_1$–$C_{12}$-alkyl, $C_3$–$C_5$-alkenyl, $C_1$–$C_{18}$-acyl or $C_7$–$C_{12}$-aralkyl, $R^{22}$ and $R^{23}$ independently of one another are hydrogen, $C_1$–$C_{12}$-alkyl, $C_3$–$C_5$-alkenyl, phenyl or cyclohexyl, $R^{24}$ is $C_1$–$C_{12}$-alkyl, $R^{25}$ is hydrogen or $C_1$–$C_{12}$-alkyl, $R^{26}$ is $C_1$–$C_4$-alkyl, $C_1$–$C_{12}$-alkoxy, phenyl, benzyl or phenoxy, $R^{27}$ is $C_1$–$C_4$-alkyl or phenyl, r is a number 1 to 4, q is the number 0 or 1, k is a number 4 to 11, Y is ethylene, 1,4-but-2-enylene or o-, p- or m-xylylene, z is a group of the formulae —O—$R^{28}$—O—, —OC(O)—$R^{29}$—C(O)O—, —$N(R^{30})$—C(O)—$R^{31}$—C(O)—$N(R^{30})$—, —$N(R^{30})$—C(O)—$N(R^{30})$, —C(O)O—$R^{31}$—OC(O)— or

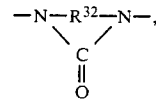

$R^{28}$ is $C_2$–$C_{20}$-alkylene, o-, m- or p-xylylene or 1,2-, 1,3- or 1,4-dimethylenecyclohexylene, $R^{29}$ is $C_2$–$C_{20}$-alkylene, o-, m- or p-phenylene or $C_8$–$C_{12}$-arylenedialkylene, $R^{30}$ is hydrogen, $C_1$–$C_{12}$-alkyl, $C_7$–$C_{12}$-aralkyl, $C_5$–$C_8$-cycloalkyl or phenyl which is unsubstituted or substituted by $C_1$–$C_4$-alkyl, $R^{31}$ is $C_2$–$C_{20}$-alkylene or o-, m- or p-phenylene or 1,2-, 1,3- or 1,4-cyclohexylene, each of which is unsubstituted or substituted by $C_1$–$C_4$-alkyl, and $R^{32}$ is ethylene or propylene, and to acid addition salts thereof.

Any alkyl substituents are straight-chain or branched alkyl groups. $C_1$–$C_4$-alkyl is, for example, methyl, ethyl, n-propyl, isopropyl, n-butyl, sec.-butyl or tert.-butyl. $C_1$–$C_6$-alkyl can additionally be, for example, n-pentyl, 2,2-dimethylpropyl, n-hexyl and 2,3-dimethylbutyl. $C_1$–$C_{12}$-alkyl can additionally be, for example, n-octyl, 1,1,3,3-tetramethylbutyl, n-nonyl, decyl or dodecyl. $C_1$–$C_{20}$-alkyl can additionally be, for example, tetradecyl, hexadecyl, heptadecyl, octadecyl or eicosyl.

A $C_6$–$C_{10}$-aryl radical A can be, for example, naphthyl and preferably phenyl.

Any $C_3$–$C_5$-alkenyl substituents are, for example, allyl, methallyl, 2-butenyl or 2-pentenyl. Allyl is preferred. $C_2$–$C_{12}$-alkenyl radicals A and A' are additionally, for example, vinyl, 2-hexenyl, 2-octenyl or 2-dodecenyl. Vinyl is preferred.

$C_3$–$C_5$-alkynyl radicals $R^9$, $R^{12}$ and $R^{14}$ are, for example, propargyl, 1-butynyl, 2-butynyl or n-1-pentynyl. Propargyl is preferred.

Any $C_5$–$C_8$-cycloalkyl substituents are, for example, cyclopentyl, cycloheptyl, cyclooctyl and, in particular, cyclohexyl.

$C_1$–$C_4$-alkoxy radicals A and $R^{10}$ are, for example, methoxy, ethoxy, isopropoxy or butoxy. $C_1$–$C_{12}$-alkoxy radicals $R^{11}$ and $R^{26}$ can additionally be, for example, also hexyloxy, octyloxy or dodecyloxy.

Any $C_7$–$C_{12}$-aralkyl substituents are, for example, phenalkyl or naphthalkyl, the alkyl moiety in the case of phenalkyl consisting in each case of branched or unbranched $C_1$–$C_6$-alkyl, but particularly $C_1$–$C_4$-alkyl. Preferred phenalkyl radicals are α,α-dimethylbenzyl, 1-phenylethyl, 2-phenylethyl and benzyl. Examples of naphthalkyl radicals are 1-naphthylmethyl, 1-naphthylethyl, 2-naphthylmethyl and 2-naphthylethyl.

A $C_7$–$C_{30}$-alkaryl radical A is, for example, phenyl or naphthyl which is monosubstituted to trisubstituted by alkyl, the alkyl moiety consisting in each case of branched or unbranched $C_1$–$C_{12}$-alkyl. Examples of alkaryl radicals are tolyl, 2,4-dimethylphenyl, 2,6-dimethylphenyl, 2,4-diethylphenyl, 2,6-diethylphenyl, 2,4-di-tert.-butylphenyl, 2,6-di-tert.-butylphenyl, 2,4,6-triisopropylphenyl or 4-tert.-butylphenyl. p-Tolyl, p-isopropylphenyl, p-dodecylphenyl, 2,4,6-trimethylphenyl and di-nonylnaphthyl are preferred.

A camphoryl radical A is preferably camphor-10-yl.

$C_1$–$C_{18}$-acyl radicals $R^9$, $R^{12}$, $R^{15}$ and $R^{21}$ are, for example, the radicals of acetic, propionic, butyric, isovaleric, acrylic, methacrylic, caproic, caprylic, lauric, palmitic, oleic, stearic, benzoic, 4-chlorobenzoic, 4-octylbenzoic, toluic, phenoxyacetic, salicylic, 2-phenylpropionic, cyclohexanecarboxylic, furan-2-carboxylic, dimethylcarbamic, diphenylcarbamic, cyclohexylcarbamic or diphenylphosphinic acid. Acetyl and acryloyl are preferred.

$C_2$–$C_{20}$-alkylene radicals A', $R^{28}$, $R^{29}$ and $R^{30}$ are, for example, 1,2-ethylene, 1,3-propylene, tetramethylene, hexamethylene, octamethylene, dodecamethylene or octadecamethylene.

$R^{19}$ and $R^{20}$ together can be $C_4$–$C_{11}$-alkylene. They then form, together with the C atom to which they are attached, a cycloalkane ring, for example a cyclopentane, cyclohexane, cyclooctane or cyclododecane ring.

A $C_6$–$C_{12}$-arylene radical A' is, for example, phenylene, naphthylene or diphenylene. m-Phenylene is preferred.

A $C_7$–$C_{28}$-alkylarylene radical A' can be, for example, methylphenylene, dimethylphenylene or dinonylnaphthylene.

$C_2$–$C_4$-hydroxyalkyl radicals $R^9$, $R^{12}$ and $R^{15}$ can be, for example, 2-hydroxyethyl, 3-hydroxypropyl or 4-hydroxybutyl. 2-Hydroxyethyl is preferred.

A $C_3$–$C_{10}$-alkoxycarbonylalkyl radical $R^9$ is, for example, methoxycarbonylmethyl, ethoxycarbonylmethyl, isopropoxycarbonylmethyl, octyloxycarbonylmethyl, methoxycarbonylethyl, ethoxycarbonylethyl or butoxycarbonylethyl.

A $C_3$–$C_5$-alkenyloxy radical $R^{11}$ is, for example, allyloxy, methallyloxy, 2-butenyloxy or 2-pentenyloxy.

A $C_1$–$C_{12}$-acyloxy radical $R^{11}$ is, for example, formyloxy, acetoxy, propionyloxy, butyroyloxy, hexanoyloxy, octanoyloxy or lauroyloxy.

A $C_1$–$C_{12}$-acylamino radical $R^{11}$ can be, for example, formylamino, acetylamino, propionylamino, butyroylamino, hexanoylamino, octanoylamino or lauroylamino.

A $C_2$–$C_{14}$-alkoxycarbonyl radical $R^{11}$ is, for example, methoxycarbonyl, ethoxycarbonyl, butoxycarbonyl or dodecyloxycarbonyl.

A $C_8$–$C_{12}$-arylenedialkylene radical $R^{29}$ can be, for example, xylylene or phenylene-1,4-diethylene.

Compounds of the formula I which are of particular interest are those in which m is the number 1 or 2, X is a direct bond or a group of the formula III in which $R^1$, $R^2$ and $R^3$ are hydrogen, A is $C_1$–$C_{18}$-alkyl, methoxy, vinyl, amino, phenyl, naphthyl, phenyl or naphthyl which is monosubstituted or disubstituted by $C_1$–$C_{12}$-alkyl, 2,4,6-trimethylphenyl, camphor-10-yl, a group of the formula —$(CH_3)_2$—$CH_2$—NH—C(O)—CH=$CH_2$ or a group of the formula

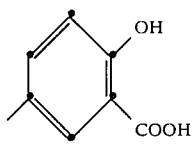

and B, provided that m=1, is a group of the formulae IV and V, and, if m=1 and if X is a group of the formula III, is, in addition, also a group of the formulae XI and XIV, and, if m=2, is a group of the formulae XVIII and XX, and, if m=2 and if X is a group of the formula III, is, in addition, also a group of the formula XXI, and, in the formulae IV, V, XI, XIV, XVIII, XX and XXI, R is hydrogen, $R^9$ is hydrogen, $C_1$–$C_6$-alkyl, allyl, benzyl, acetyl, acryloyl, 2-hydroxyethyl, cyanomethyl or oxyl, $R^{10}$ is hydrogen, methyl, phenyl or phenoxymethyl, $R^{11}$ is hydrogen, $C_1$–$C_4$-alkoxy, allyloxy, $C_1$–$C_{12}$-acyloxy, $C_1$–$C_{12}$-acylamino, $C_2$–$C_6$-alkoxycarbonyl or a group of the formula

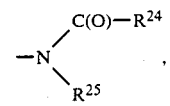

$R^{12}$ is hydrogen or $C_1$–$C_4$-alkyl, $R^{13}$ is hydrogen, $R^{14}$ is hydrogen, $C_1$–$C_{12}$-alkyl, allyl or benzyl, $R^{15}$ is hydrogen, methyl or benzyl, $R^{16}$ is hydrogen, methyl or ethyl, $R^{17}$ and $R^{18}$ are $C_1$–$C_4$-alkyl, $R^{19}$ and $R^{20}$ are hydrogen or $C_1$–$C_6$-alkyl or, together, are $C_4$–$C_{11}$-alkylene, $R^{24}$ is $C_1$–$C_{12}$-alkyl, $R^{25}$ is hydrogen or $C_1$–$C_{12}$-alkyl and Z is a group of the formulae —OC(O)—$R^{29}$—C(O)O— or —N($R^{30}$)—C(O)—$R^{31}$—C(O)—N($R^{30}$)— in which $R^{29}$ is $C_2$–$C_{10}$-alkylene or o-, m- or p-phenylene, $R^{30}$ is hydrogen, $C_1$–$C_{12}$-alkyl or benzyl and $R^{31}$ is $C_2$–$C_{10}$-alkylene or o-, m- or p-phenylene, and acid addition salts thereof.

Compounds of the formula I which are of very particular interest are those in which m is the number 1 or 2, X is a direct bond or a group of the formula III in which $R^1$, $R^2$ and $R^3$ are hydrogen, A is methyl, ethyl, $C_{14}$–$C_{17}$-alkyl, methoxy, vinyl, amino, phenyl, p-methylphenyl, p-isopropylphenyl, p-dodecylphenyl, naphthyl, dinonylnaphthyl, camphor-10-yl, a group of the formula —$C(CH_3)_2$—$CH_2$—NH—C(O)—CH=$CH_2$ or a group of the formula

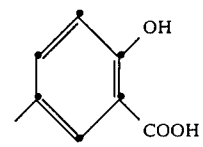

and B, provided that m=1, is a group of the formulae IV and V and, if m=1 and if X is a group of the formula III, is, in addition, also a group of the formula XI and, if m=2, is a group of the formula XVIII and, if m=2 and if X is a group of the formula III, is, in addition, also a group of the formula XXI, and, in the formulae IV, V, XI, XVIII and XXI, R is hydrogen, $R^9$ is hydrogen, $C_1$–$C_6$-alkyl, allyl, benzyl, oxyl, acetyl, acryloyl, β-hydroxyethyl or cyanomethyl, $R^{10}$ is hydrogen, methyl or phenyl and $R^{11}$ is hydrogen or $C_1$–$C_4$-alkoxy, and acid addition salts thereof.

Compounds of the formula I which are preferred amongst these are those in which m is the number 1, B is a group of the formula IV, X is a direct bond or a group of the formula —O—$CH_2$—CH(OH)—$CH_2$— and A is as defined above.

Some examples of compounds, according to the invention, of the formulae I and II are listed in Tables 1 and 2 below.

4,537,923
TABLE 1
| B | B―(X―OSO₂―A)ₘ | | |
|---|---|---|---|
| | X | A | m |
| 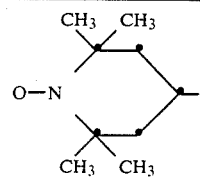 | direct bond | 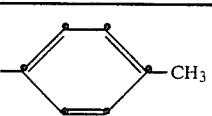 | 1 |
| 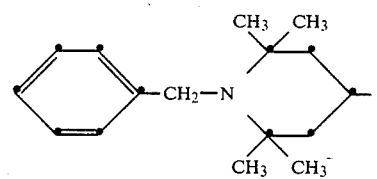 | direct bond | 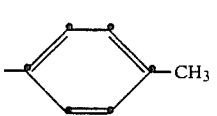 | 1 |
| 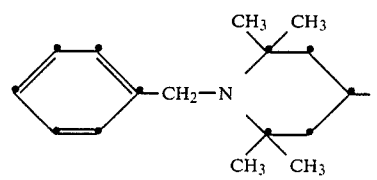 | direct bond | —CH₃ | 1 |
|  | direct bond | 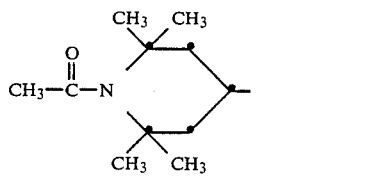 | 1 |
| 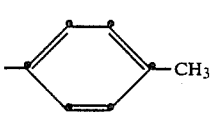 | direct bond | 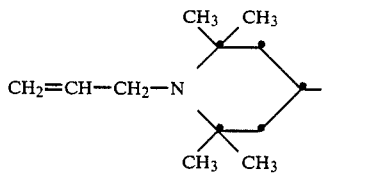 | 1 |
| 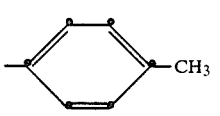 | —O—CH₂—CH—CH₂—<br>                OH | 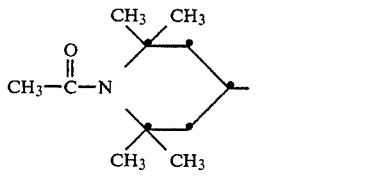 | 1 |
|  | direct bond | —OCH₃ | 1 |
| 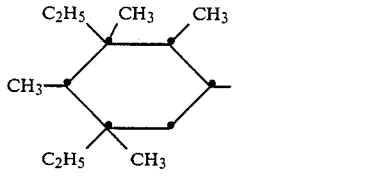 | direct bond |  | 1 |

TABLE 1-continued

| B | $\underline{B(\!-\!X\!-\!OSO_2\!-\!A)_m}$ X | A | m |
|---|---|---|---|
| $CH_3SO_3^\ominus$ [2,2,6,6-tetramethylpiperidinium with H,H on N⊕] | direct bond | $-CH_3$ | 1 |
| $Cl^\ominus$ [2,2,6,6-tetramethylpiperidinium with H,H on N⊕] | direct bond | phenyl | |
| [2,2,6,6-tetramethylpiperidine N-CH₂-CH(CH₃)-CH₂-] | direct bond | $-CH_3$ | 2 |
| [bis(2,2,6,6-tetramethylpiperidino)-N-CH₂-CH₂-N] | direct bond | 4-methylphenyl | 2 |
| HN-[2,2,6,6-tetramethylpiperidine] | direct bond | camphor-10-yl | 1 |
| phenyl-CH₂-N-[2,2,6,6-tetramethylpiperidine] | $-O-CH_2-CH(OH)-CH_2-$ | 4-methylphenyl | 1 |
| $CH_3-N$-[2,2,6,6-tetramethylpiperidine] | $-O-CH_2-CH(OH)-CH_2-$ | 4-methylphenyl | 1 |
| $CH_2\!=\!CH\!-\!\overset{O}{\underset{\|}{C}}\!-\!N$-[2,2,6,6-tetramethylpiperidine] | direct bond | $-C_2H_5$ | 1 |

4,537,923

TABLE 1-continued

| B | B−(X−OSO₂−A)ₘ | | m |
|---|---|---|---|
| | X | A | |
| HO−CH₂−CH₂−N<piperidine(2,2,6,6-tetramethyl)> | direct bond | −C₆H₄−C₁₂H₂₅ | 1 |
| CH₃−N<piperidine(2,2,6,6-tetramethyl)> | direct bond | −NH₂ | 1 |
| NC−CH₂−N<piperidine(2,2,6,6-tetramethyl)> | direct bond | −C₆H₄−CH(CH₃)₂ | 1 |
| CH₃−N<piperidine(2,2,6,6-tetramethyl)> | direct bond | −C₆H₃(OH)(COOH) | 1 |
| −CH₃−N<piperidine(2,2,6,6-tetramethyl)> | direct bond | −CH=CH₂ | 1 |
| CH₃−N<piperidine(2,2,6,6-tetramethyl)> | direct bond | −C₁₄₋₁₇H₂₉₋₃₅ | 1 |
| H−N<piperidine(2,2,6,6-tetramethyl)> | direct bond | −C(CH₃)₂−CH₂−NH−C(O)−CH=CH₂ | 1 |
| H−N<piperidine(2,2,6,6-tetramethyl)> | direct bond | −C₆H₄−N(maleimide) | 1 |

TABLE 2

$(B'-X-OSO_2)_{\overline{n}}A'$

| B' | X | A' |
|---|---|---|
| 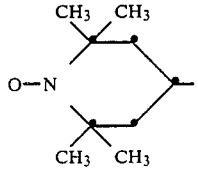 | direct bond | 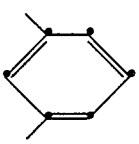 |
| 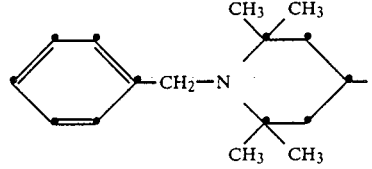 | direct bond | —CH₂—CH₂— |
| 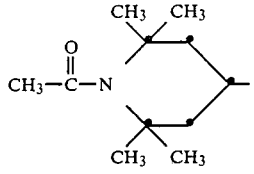 | direct bond | $(CH_2)_{\overline{6}}$ |
| 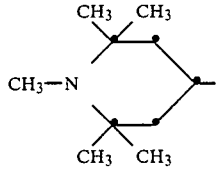 | direct bond | 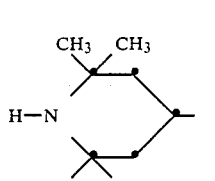 |
| 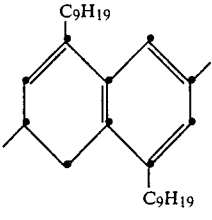 | —O—CH₂—CH(OH)—CH₂— | —CH₂—CH₂— |

The preparation of the compounds, according to the invention, of the formulae I and II is effected in analogy with processes known per se, for example (a) by reacting an alcohol of the formula

B—OH                                                (XXVII)

with a sulfonic acid halide, in particular a chloride, of the formula

A—SO₂Cl                                    (XXVIII)

in a molar ratio of 1:1, or reacting an alcohol of the formula

B'—OH                                             (XXIX)

with a disulfonic acid halide, in particular a chloride, of the formula

Cl—O₂S—A—SO₂—Cl in a molar ratio of 2:1, in an inert solvent, in the presence of a base as proton acceptor, at a temperature between 0° and 100° C., preferably 20° and 50° C., A, B and B' in the formulae XXVII—XXIX being as defined above. Suitable bases are tertiary amines, such as trialkylamines, pyridine, alkali metal hydroxides or carbonates and alkaline earth metal hydroxides. It is also possible, however, to employ a corresponding excess (1 or 2 mols) of the polyalkylpiperidine base to be esterified, one half being esterified and the other acting as a proton acceptor;

(b) by reacting an alcohol of the formula XXVII with a sulfonic acid anhydride of the formula

                       (XXX)

in an inert solvent, with the formation of compounds of the formula I and of the formula A—SO₂OH, A and B being as defined above;

(c) by reacting an alcohol of the formula XXVII with a sulfonic acid ester of the formula

A—SO₂OR³³                                 (XXXI)

in a molar ratio of 1:1, or reacting an alcohol of the formula XXIX with a disulfonic acid ester of the formula

$$R^{33}OSO_2-A'-SO_2OR^{33} \qquad (XXXII)$$

in a molar ratio of 2:1, or reacting a diol of the formula

$$HO-B-OH \qquad (XXXIII)$$

with a sulfonic acid ester of the formula XXXI in a molar ratio of 1:2, in the presence of a titanium compound of the formula Ti(OR$^{34}$)$_4$, A, A', B and B' being as defined above and R$^{33}$ and R$^{34}$ being C$_1$–C$_4$-alkyl; or (d) by reacting a monoepoxide of the formula

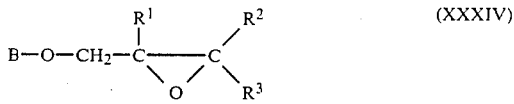
(XXXIV)

with a sulfonic acid of the formula

$$A-SO_2-OH \qquad (XXXV)$$

in a molar ratio of 1:1, or reacting a monoepoxide of the formula

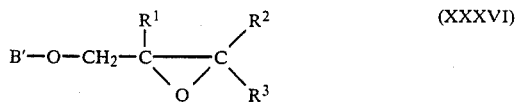
(XXXVI)

with a disulfonic acid of the formula

$$HO-O_2S-A'-SO_2-OH \qquad (XXXVII)$$

in a molar ratio of 2:1, or reacting a diepoxide of the formula

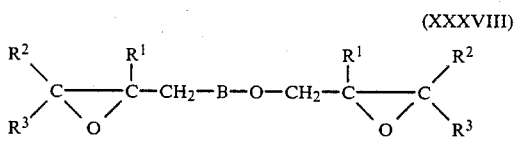
(XXXVIII)

with a sulfonic acid of the formula XXXV in a molar ratio of 1:2, in an inert solvent.

The starting materials are known. If any of them should be novel, they can be prepared in analogy with methods known per se and they also constitute a subject of the invention.

Acid addition salts are obtained by reacting, with acids, the polyalkylpiperidinesulfonic acid esters according to the invention, which contain a basic polyalkylpiperidine group. Examples of suitable acids are inorganic acids, for example hydrochloric acid, phosphoric acid or amidosulfonic acid or, in particular, organic acids, for example monosulfonic or polysulfonic acids, for example methanesulfonic acid, methylamidosulfonic acid, ethanesulfonic acid, 2-ethylhexanesulfonic acid, vinylsulfonic acid, benzenesulfonic acid, toluenesulfonic acids, naphthalenesulfonic acids, benzenedisulfonic acids, naphthalenedisulfonic acids, styrenesulfonic acid, alkylated benzenesulfonic or naphthalenesulfonic acids, technical mixtures or paraffinsulfonic acids, acrylamido-N-alkanesulfonic acids, polystyrenepolysulfonic acids or polyvinylsulfonic acid; acid phosphoric acid esters, for example phenylphosphoric acid or diethylphosphoric acid; phosphonic and phosphinic acids, for example methylphosphonic acid, phenylphosphonic acid, dodecylphenylphosphonic acid, phenylbutylphosphinic acid, diphenylphosphinic acid or methylbenzylphosphinic acid; phosphonic acid monoesters, for example methyl methylphosphonate or ethyl phenylphosphonate; maleic acid and monoesters thereof, for example monobutyl maleate or monohexyl maleate; and phthalic acid and monoesters thereof, for example monohexyl phthalate.

The invention also relates to the use of the compounds of the formulae I and II as curing catalysts for acid-curable resins, in which connection they act at the same time as light stabilisers in these resins, and to the acid-curable resins containing the compounds according to the invention.

The polyalkylpiperidinesulfonic acid esters of the formulae I and II are added to the resins in a quantity adequate for curing. The quantity required depends not only on the nature of the resin but also on the intended curing temperature and curing time. In general, 0.1 to 10% by weight, preferably 0.5 to 5% by weight, based on the solvent-free resin, are used. These quantities also ensure an adequate light stabilising effect by the piperidinesulfonic acid esters. It is also possible to employ mixtures of compounds of the formulae I and II. The addition of the piperidinesulfonic acid esters to the finish is effected merely by mixing with the remaining components of the finish. The ester can also be added in a dissolved form to the finish. This is particularly advantageous if the ester is obtained in the form of a solution when it is prepared, so that it is not necessary to isolate it.

Suitable acid-curable resins are any resins, the curing of which can be accelerated by means of acid catalysts. These are, in particular, finishes based on acrylic, polyester, alkyd, melamine, urea and phenolic resins, but especially mixtures of acrylic, polyester or alkyd resins with one another or with a melamine resin. These also include modified surface-coating resins, for example acrylic-modified polyester or alkyd resins. Examples of individual types of resins which fall under the definition acrylic, polyester and alkyd resins are described, for example, in Wagner, Sarx/Lackkunstharze ("Synthetic Resins for Finishes") (Munich, 1971), pages 86 to 123 or 229 to 238, or in Ullmann/Encyclopädie der techn. Chemie ("Encyclopedia of Industrial Chemistry"), 4th Edition, Volume 15 (1978), pages 613 to 628. Acid catalysis is particularly important for the curing of finishes containing etherified amino resins, for example methylated or butylated melamine resins (N-methoxymethylmelamine or N-butoxymethylmelamine) or methylated/butylated glycol urils and the like, for example:

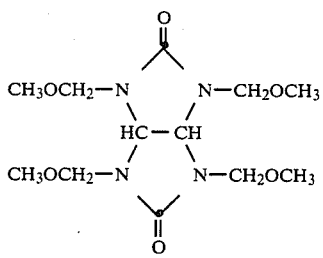

Further resin compositions are mixtures of polyfunctional alcohols or acrylic and polyester resins containing hydroxyl groups, or partially saponified polyvinyl acetate or polyvinyl alcohol containing polyfunctional dihydropyranyl ethers, for example derivatives of 3,4-dihydro-2H-pyran-2-carboxylic acid. Resins which are particularly preferred for the use of the piperidinesulfonic acid esters according to the invention are those which contain an acrylate component and are cured with completely etherified melamine resins.

For specific purposes, use is also made of resin compositions which have monomeric or oligomeric constituents containing polymerisable unsaturated groups. Resin compositions of this type can also be cured by means of the compounds according to the invention. In this connection it is also possible to use concomitantly free radical polymerisation initiators or photoinitiators, for example those belonging to the class comprising the aromatic ketones, benzoin compounds, benzyl ketals of α-hydroxyacetophenone derivatives. In addition to the polymerisation of the unsaturated components, however, an acid-catalysed crosslinking (if necessary when stoving) must always be carried out.

The finishes can be solutions or dispersions of the surface-coating resin in an organic solvent or in water, but they can also be solvent-free. Finishes of particular interest are those having a low solvent content, so-called "high solids finishes". The finishes can be clear finishes, such as are used, for example, in the automobile industry as topcoats for multi-coat paints. They can also contain pigments, both inorganic and organic pigments, and also metal powders for metallic-effect finishes.

The finishes can also contain minor quantities of special additives such as are customary in surface-coating technology, for example flow control auxiliaries, thixotropic agents of antioxidants. Although the piperidinesulfonic acid esters according to the invention are excellent light stabilisers, it can in certain cases be advantageous to use concomitantly, in addition, other light stabilisers, for example light-stabilisers of the type of UV absorbers or organic nickel compounds, because synergistic effects can be produced thereby. Examples of classes of UV absorbers which can be used are the hydroxyphenylbenztriazoles, the hydroxybenzophenones, the oxalanilides, the cyanoacrylates and the hydroxyphenyl-s-triazines. Examples of organic nickel compounds are nickel salts of phosphoric acid monoesters or Ni complexes of bisphenols. It is particularly preferable to use concomitantly hydroxyphenylbenztriazole light stabilisers, for example 2-(2-hydroxy-3,5-di-t.-amylphenyl)-benztriazole or 2-[2-hydroxy-3,5-di-(α-dimethylbenzyl)-phenyl]-benztriazole.

The finishes are applied by the customary methods of industrial finishing to the substrates to be coated, for example by brushing, spraying or dipping.

The finishes are dried and baked after being applied. The curing temperatures can be 80° to 300° C. for curing times of a few seconds up to one hour. Low curing temperatures from about 100° to 150° C., such as are used for touching-up finishes on automobiles or in the case of other finishing operations carried out on sensitive industrial articles, are of particular interest for the use of the compounds according to the invention.

The use of finishes containing compounds according to the invention is suitable for all types of industrial finishing, for example for the finishing of machines, vehicles, ships or structural components. It is of particular importance for vehicle finishing. This can be either single-coat finishing or multi-coat finishing. The use of finishes containing the compounds according to the invention is also of particular interest for the continuous coating of metal sheet, for example steel or aluminium sheet, the so-called coil coating process.

The invention is described in greater detail below by means of a few typical examples.

EXAMPLE 1

11.7 g (0.102 mol) of methanesulfonyl chloride in 50 ml of toluene are added dropwise, at room temperature and in the course of half an hour and while stirring, to a solution of 24.74 g (0.1 mol) of 1-benzyl-4-hydroxy-2,2,6,6-tetramethylpiperidine and 20.2 g (0.2 mol) of triethylamine in 60 ml of toluene, in the course of which the temperature rises to approximately 70° C. The mixture is then stirred for a further 20 hours at room temperature. The reaction mixture is evaporated at 40° C. on a rotary evaporator under a water pump vacuum, the residue is dissolved in methylene chloride, the solution is washed several times with water and the organic phase is dried over sodium sulfate and evaporated. The crude compound is recrystallised in cyclohexane, thereby affording 4-methanesulfonyloxy-1-benzyl-2,2,6,6-tetramethylpiperidine as a colourless crystalline powder of melting point 104°–106° C. (Compound No. 1).

The following compounds are prepared analogously: 1-benzyl-4-p-toluenesulfonyloxy-2,2,6,6-tetramethylpiperidine, melting point 103°–104° C. (Compound No. 2), 1-allyl-4-p-toluenesulfonyloxy-2,2,6,6-tetramethylpiperidine, melting point 82°–83° C. (Compound No. 3), 1-acetyl-4-p-toluenesulfonyloxy-2,2,6,6-tetramethylpiperidine, melting point 104°–105° C. (Compound No. 4), 4-p-toluenesulfonyloxy-1,2,2,6,6-pentamethylpiperidine, melting point 73° C. (Compound No. 5).

EXAMPLE 2

A solution of 17.2 g (0.1 mol) of 4-hydroxy-2,2,6,6-tetramethylpiperidine 1-oxide in 130 ml of pyridine is treated, at approximately 0° C. and while stirring, with 19.1 g (0.1 mol) of p-toluenesulfonyl chloride, in portions. The mixture is then stirred for a further 24 hours at approximately 20° C. The sulfonic acid ester is isolated by freeing the reaction mixture substantially from pyridine, in vacuo at 45° C., on a rotary evaporator, dissolving the residue in methylene chloride and extracting the solution repeatedly with water. The organic phase is dried over sodium sulfate and the solvent is removed by distillation. The residue is stirred vigorously with hexane at 40°–50° C. for one hour, the hexane solution is filtered and evaporated, and the residue is recrystallised in diisopropyl ether, thereby affording 4-p-toluenesulfonyloxy-2,2,6,6-tetramethylpiperidine 1-oxide of melting point 112°–114° C. (Compound No. 6).

The following are prepared analogously: 4-methanesulfonyloxy-1,2,2,6,6-pentamethylpiperidine, boiling point 80° C./0.13 Pa (Compound No. 7) and 1-[2-(p-toluenesulfonyloxy)-ethyl]-2,2,6,6-tetramethylpiperidine, melting point 106°–108° C. (Compound No. 8).

EXAMPLE 3

15.2 g of 4-(2,3-epoxypropoxy)-1-benzyl-2,2,6,6-tetramethylpiperidine are added to 9.6 g of p-toluenesulfonic acid in 50 ml of toluene. The mixture is warmed to 80° C. under nitrogen. It is allowed to react for 2 hours at this temperature. A thin layer chromatogram shows that starting material is no longer present. The pale yellow solution is then cooled. Two liquid layers are formed. The addition of approximately 100 ml of methylene chloride gives a homogeneous pale yellow solution, which is dried over anhydrous MgSO₄. The organic solution is then evaporated completely and the residue is dried at 40°–45° C. under a high vacuum. This gives 23.5 g of 2-hydroxy-3-(1-benzyl-2,2,6,6-tetramethyl-4-piperidyloxy)-propyl p-toluenesulfonate (Compound No. 9) in the form of a slightly orange-coloured resin.

| Analysis: | |
|---|---|
| Calculated: C 65.66% | Found: C 65.48% |
| H 7.84% | H 8.20% |
| N 2.94% | N 2.83% |
| S 6.74% | S 6.38% |

The following sulfonic acid esters are prepared from the corresponding glycidyl ethers: 2-hydroxy-3-(1,2,2,6,6-pentamethyl-4-piperidyloxy)-propyl p-toluenesulfonate, amorphous resin (Compound No. 10), 2-hydroxy-3-(1,2,2,6,6-pentamethyl-4-piperidyloxy)-propyl p-dodecylbenzenesulfonate, amorphous resin, (Compound No. 11), 2-hydroxy-3-(1-benzyl-2,2,6,6-tetramethyl-4-piperidyloxy)-propyl p-dodecylbenzenesulfonate, amorphous resin (Compound No. 12), 2-hydroxy-3-(1-acetyl-2,2,6,6-tetramethyl-4-piperidyloxy)-propyl p-toluenesulfonate, viscous oil (Compound No. 13), 2-hydroxy-3-(4-hydroxy-2,2,6,6-tetramethylpiperidino)-propyl p-dodecylbenzenesulfonate, amorphous resin (Compound No. 14).

EXAMPLE 4-Preparation of the glycidyl ether 30.3 g (0.3 mol) of 4-hydroxy-1-benzyl-2,2,6,6-tetramethylpiperidine are dissolved in 250 ml of toluene. 84 g (1.5 mols) of solid powdered KOH and 5 mol % of 18-crown-6 are added to the solution. The mixture is warmed to 70° C. and a solution of 50 g (0.5 mol) of epichlorohydrin dissolved in 50 ml of toluene is added slowly at this temperature. The reaction is very exothermic. The internal temperature should not exceed 75°–80°. As time goes on, the reaction solution turns a brownish colour. The conversion is followed by means of gas chromatography. After dropwise addition has been carried out for approximately 1 hour, the mixture is stirred for a further 2 hours at 75°–80° C. to complete the reaction. The reaction solution is then cooled and treated with water. The toluene phase is separated off and evaporated. The residue is distilled under a high vacuum. This gives 50.1 g of 4-(2,3-epoxypropoxy)-1-benzyl-2,2,6,6-tetramethylpiperidine. Boiling point 137°–140° C./6.66 Pa.

A procedure in other respects as described above is followed, using the piperidines below instead of 4-hydroxy-1-benzyl-2,2,6,6-tetramethylpiperidine, the following being obtained:

From 4-hydroxy-1,2,2,6,6-pentamethylpiperidine: 4-(2,3epoxypropoxy)-1,2,2,6,6-pentamethylpiperidine, boiling point 68°–69° C./0.666 Pa.

From 4-hydroxy-1-allyl-2,2,6,6-tetramethylpiperidine: 4-(2,3-epoxypropoxy)-1-allyl-2,2,6,6-tetramethylpiperidine, boiling point 88°–90° C./1.333 Pa.

From 4-hydroxy-1-acetyl-2,2,6,6-tetramethylpiperidine: 4-(2,3-epoxypropoxy)-1-acetyl-2,2,6,6-tetramethylpiperidine, boiling point 110° C./13.332 Pa.

From 4-hydroxy-1-(2-hydroxypropyl)-2,2,6,6-tetramethylpiperidine: 4-(2,3-epoxypropoxy)-1-(2-hydroxypropyl)-2,2,6,6-tetramethylpiperidine, boiling point 118°–120° C./3.999 Pa.

From 4-hydroxy-2,2,6,6-tetramethylpiperidine: 4-(2,3-epoxypropoxy)-2,2,6,6-tetramethylpiperidine, boiling point 54° C./1.333 Pa.

From 4-hydroxy-1-(2,3-epoxypropyl)-2,2,6,6-tetramethylpiperidine: 4-(2,3-epoxypropoxy)-1-(2,3-epoxypropyl)-2,2,6,6-tetramethylpiperidine, boiling point 120° C./0.666 Pa.

From 4-hydroxy-1-(2-hydroxyethyl)-2,2,6,6-tetramethylpiperidine: 4-(2,3-epoxypropoxy)-1-(5,6-epoxy-3-oxahexyl)-2,2,6,6-tetramethylpiperidine, boiling point 150°–155° C./0.666 Pa.

From 1-(2-hydroxyethyl)-2,2,6,6-tetramethylpiperidine: 1-(5,6-epoxy-3-oxahexyl)-2,2,6,6-tetramethylpiperidine, boiling point 88°–90° C.

EXAMPLE 5

Curing an acrylic/melamine resin finish

A clear lacquer having the following formulation is prepared:

| | |
|---|---|
| 57.30 g | of a hydroxyl-functional acrylic resin (Paraloid ® AT 410, Rohm & Haas, USA), |
| 17.93 g | of hexamethoxymethylmelamine (Cymel ® 301, American Cyanamid), |
| 1.83 g | of cellulose acetobutyrate (CAB 551.001, Eastman Chem. Co.), |
| 2.80 g | of a flow control auxiliary based on a silicone resin (Byketol ® Spezial, Byk-Mallinckrodt, West Germany), |
| 0.29 g | of a flow control auxiliary based on a surfactant (Modaflow ®, Monsanto, USA), |
| 10.12 g | of butanol and |
| 9.73 g | of butyl acetate |
| 100.00 g | |

This finish has a solids content of 59.76%. Samples of this finish are mixed with various curing catalysts in the quantities indicated in Table 1 and 2 and are applied, in a dry film thickness of approx. 40 μm, to aluminium sheets coated with a white coil-coat. Curing is carried out for 30 minutes at 100° C. The degree of curing is assessed by determining the König pendulum hardness (DIN 53,157), 30 minutes after stoving.

Discoloration (yellowing) is assesed by measuring the shift in shade ΔE as specified in DIN 6174 using a Hunterlab photometer.

The stability of the finish on storage is assessed by measuring its viscosity (using an ICI cone-plate viscometer) during the course of storage for 7 days at 70° C.

The results are listed in Tables 1 and 2.

TABLE 1

| Curing for 30 minutes at 120° C. | | |
|---|---|---|
| Curing catalyst (% by weight, based on solids) | Pendulum hardness (seconds) | Shift in shade ΔE |
| None | No curing | |
| 1% of p-toluenesulfonic acid | 194 | 0.1 |
| 0.5% of Compound No. 9 | 127 | 0.4 |
| 1% of Compound No. 9 | 188 | 0.2 |
| 1% of Compound No. 10 | 127 | 0.2 |
| 2% of Compound No. 10 | 119 | 0.4 |
| 1% of Compound No. 11 | 88 | 0.3 |
| 1% of Compound No. 12 | 172 | 0.2 |

TABLE 2

| Relative increase in viscosity Δη when stored for 7 days at 60° C. | |
|---|---|
| Curing catalyst | Δη (%) |
| None | 16 |
| 1% of p-toluenesulfonic acid | gelled |
| 0.5% of Compound No. 9 | 128 |
| 1% of Compound No. 9 | 140 |
| 1% of Compound No. 10 | 24 |
| 2% of Compound No. 10 | 30 |
| 1% of Compound No. 11 | 50 |
| 1% of Compound No. 12 | 600 |

What is claimed is:

1. A composition of matter containing an acid-curable resin and a compound of the formulae I $$B\text{-}(X\text{---}O\text{---}SO_2\text{---}A)_m \quad (I)$$

in which m is a number 1 to 3, X is a direct bond or a group of the formula III

  (III)@ which is attached via C* to the oxygen of the sulfo group, p being zero if the group of the formula III is attached to a nitrogen atom of B, and p otherwise being the number 1, and $R^1$, $R^2$ and $R^3$ independently of one another being hydrogen or methyl, A is $C_1\text{-}C_{20}$-alkyl, $C_1\text{-}C_4$-alkoxy, $C_2\text{-}C_{12}$-alkenyl, $C_7\text{-}C_{12}$-aralkyl, $C_6\text{-}C_{10}$-aryl, $C_7\text{-}C_{30}$-alkaryl, $C_5\text{-}C_8$-cycloalkyl, trifluoromethyl or camphoryl, each of which is unsubstituted or substituted by hydroxyl, a group —$N(R^4)(R^5)$ or —$C(CH_3)_2$—$CH_2$—$N(R^6)$—$C(O)$—$C(R^7)$=$CH_2$, in which $R^4$, $R^5$ and $R^6$ are hydrogen or $C_1\text{-}C_{12}$-alkyl and R is hydrogen or methyl, or a group of the formula

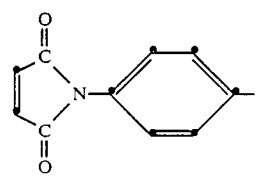

or of the formula

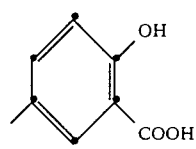

and B, provided that m=1, is a group of the formulae IV to X

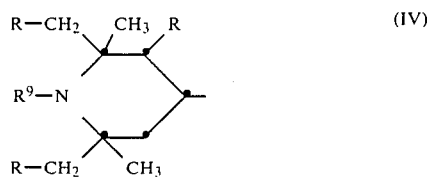  (IV)

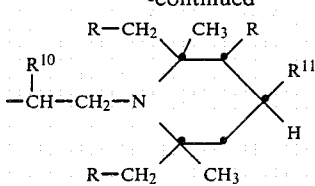  (V)

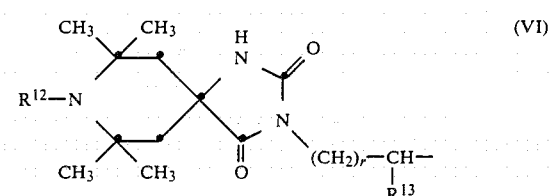  (VI)

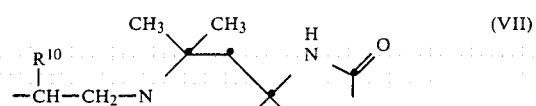  (VII)

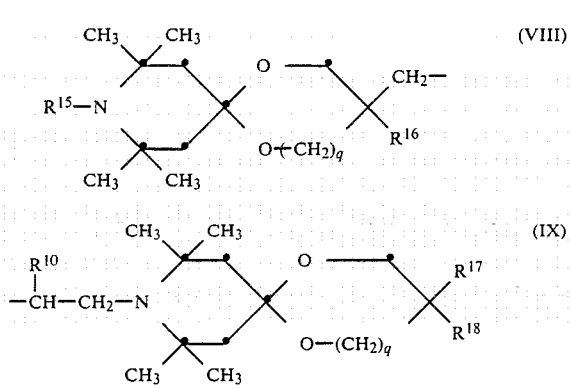  (VIII)

(IX)

(X)

in addition, B, provided that m=1, and provided that X is a group of the formula III, can also be a group of the formulae XI to XVI

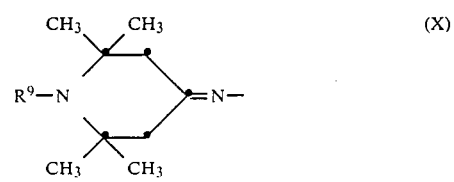  (XI)

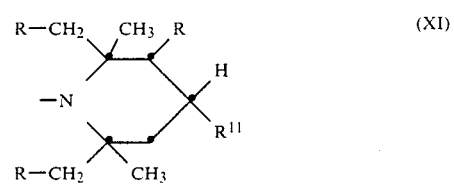  (XII)

-continued

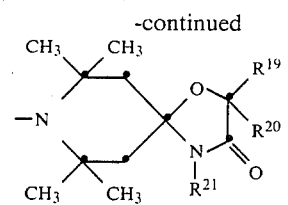 (XIII)

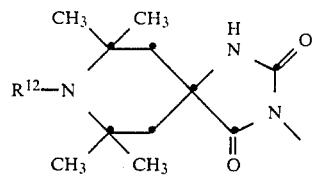 (XIV)

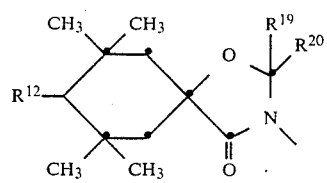 (XV)

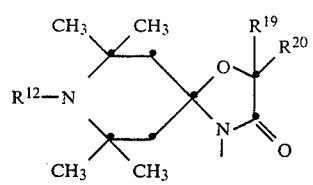 (XVI)

if m=2, B is a group of the formulae XVII to XX

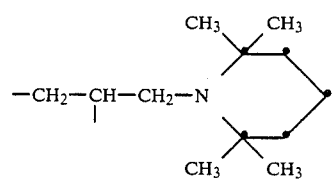 (XVII)

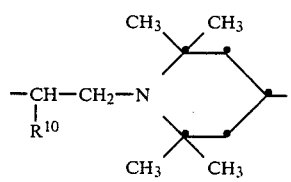 (XVIII)

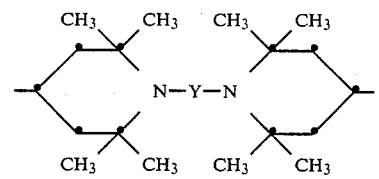 (XIX)

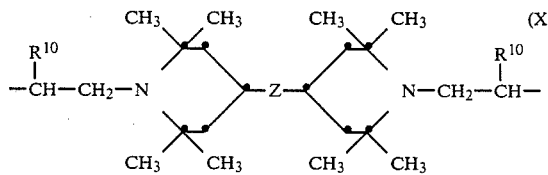 (XX)

in addition, if m=2 and if X is a group of the formula III, B can also be a group of the formulae XXI to XXV

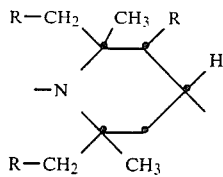 (XXI)

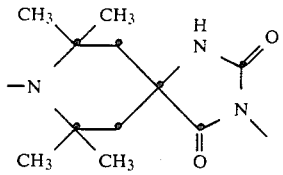 (XXII)

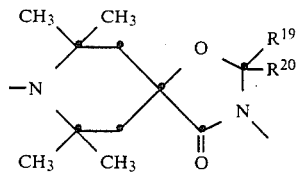 (XXIII)

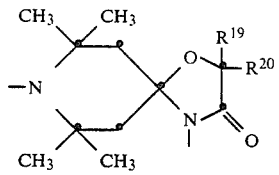 (XXIV)

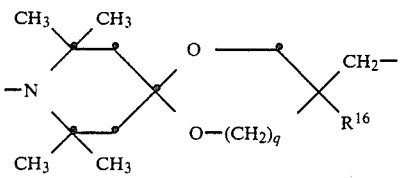 (XXV)

and, if m=3, B is a group of the formula XXVI

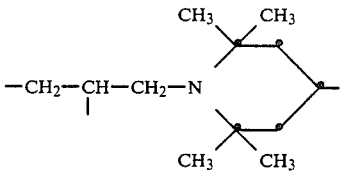 (XXVI)

and, if the formulae IV to XXV, R is hydrogen or methyl, $R^9$ is hydrogen, $C_1$–$C_{20}$-alkyl, $C_3$–$C_5$-alkenyl, $C_3$–$C_5$-alkynyl, $C_7$–$C_{12}$-aralkyl, $C_1$–$C_{18}$-acyl, $C_3$–$C_{10}$-alkoxycarbonylalkyl, $C_2$–$C_4$-hydroxyalkyl, cyanomethyl, oxyl, a group of the formula —$CH_2$—CH(OH)—$CH_2$—$OR^{27}$ or a group of the formula —C(O)—N($R^{22}$)($R^{23}$), $R^{10}$ is hydrogen, $C_1$–$C_4$-alkyl, $C_1$–$C_4$-alkoxy, phenyl, phenoxy which is unsubstituted or substituted in the phenyl nucleus by $C_1$–$C_4$-alkyl, or phenoxymethyl, $R^{11}$ is hydrogen, hydroxyl, $C_1$–$C_{12}$-alkoxy, $C_3$–$C_5$-alkenyloxy, $C_1$–$C_{12}$-acyloxy, $C_1$–$C_{12}$-acylamino, $C_2$–$C_{14}$-alkoxycarbonyl or a group of the formula

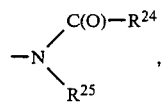

—C(O)—N($R^{24}$)($R^{25}$), —OC(O)—N($R^{24}$)($R^{25}$), or —CH$_2$—COOR$^{24}$, $R^{12}$ is hydrogen, C$_1$-C$_{12}$-alkyl, C$_3$-C$_5$ alkenyl, C$_3$-C$_5$-alkynyl, C$_7$-C$_{12}$-aralkyl, C$_1$-C$_{18}$-acyl, cyanomethyl or C$_2$-C$_4$-hydroxyalkyl, $R^{13}$ is hydrogen or C$_1$-C$_4$-alkyl, $R^{14}$ is hydrogen, C$_1$-C$_{20}$-alkyl, C$_3$-C$_5$-alkenyl C$_3$-C$_5$-alkynyl, C$_7$-C$_{12}$-aralkyl or C$_6$-C$_8$-cycloalkyl, $R^{15}$ is hydrogen, C$_1$-C$_{12}$-alkyl, C$_3$-C$_5$-alkenyl, C$_7$-C$_{12}$-aralkyl, C$_1$-C$_{18}$-acyl, cyanomethyl or C$_2$-C$_4$-hydroxyalkyl, $R^{16}$ is hydrogen, methyl or ethyl, $R^{17}$ and $R^{18}$ independently of one another are hydrogen or C$_1$-C$_6$-alkyl or $R^{17}$ and $R^{18}$ together are one of the groups of the formulae

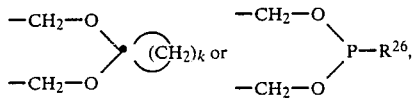

$R^{19}$ and $R^{20}$ independently of one another are hydrogen, C$_1$-C$_{12}$-alkyl, phenyl which is unsubstituted or substituted by C$_1$-C$_4$-alkyl, C$_5$-C$_8$-cycloalkyl or C$_7$-C$_{12}$-aralkyl or $R^{19}$ and $R^{20}$ together are C$_4$-C$_{11}$-alkylene, $R^{21}$ is hydrogen, C$_1$-C$_{12}$-alkyl, C$_3$-C$_5$-alkenyl, C$_1$-C$_{18}$-acyl or C$_7$-C$_{12}$-aralkyl, $R^{22}$ and $R^{23}$ independently of one another are hydrogen, C$_1$-C$_{12}$-alkyl, C$_3$-C$_5$-alkenyl, phenyl or cyclohexyl, $R^{24}$ is C$_1$-C$_{12}$-alkyl, $R^{25}$ is hydrogen or C$_1$-C$_{12}$-alkyl, $R^{26}$ is C$_1$-C$_4$-alkyl, C$_1$-C$_{12}$-alkoxy, phenyl, benzyl or phenoxy, $R^{27}$ is C$_1$-C$_4$-alkyl or phenyl, r is a number 1 to 4, q is the number 0 or 1, k is a number 4 to 11, Y is ethylene, 1,4-but-2-enylene or o-, p- or m-xylylene, z is a group of the formulae —O—R$^{28}$—O—, —OC(O)—R$^{29}$—C(O)O—, —N(R$^{30}$)—C(O)—R$^{31}$—C(O)—N(R$^{30}$)—, —N(R$^{30}$)—C(O)—C(O)—N(R$^{30}$), —C(O)O—R$^{31}$—OC(O)— or

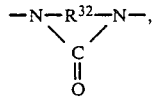

$R^{28}$ is C$_2$-C$_{20}$-alkylene, o-, m- or p-xylylene or 1,2-, 1,3- or 1,4-dimethylenecyclohexylene, $R^{29}$ is C$_2$-C$_{20}$-alkylene, o-, m- or p-phenylene or C$_8$-C$_{12}$-arylenedialkylene, $R^{30}$ is hydrogen, C$_1$-C$_{12}$-alkyl, C$_7$-C$_{12}$-aralkyl, C$_5$-C$_8$-cycloalkyl or phenyl which is unsubstituted or substituted by C$_1$-C$_4$-alkyl, $R^{31}$ is C$_2$-C$_{20}$-alkylene or o-, m- or p-phenylene or 1,2-, 1,3- or 1,4-cyclohexylene, each of which is unsubstituted or substituted by C$_1$-C$_4$-alkyl, and $R^{32}$ is ethylene or propylene, and acid addition salts thereof.

2. The composition according to claim 1 wherein m is the number 1 or 2, X is a direct bond or a group of the formula III in which $R^1$, $R^2$ and $R^3$ are hydrogen, A is C$_1$-C$_{18}$-alkyl, methoxy, vinyl, amino, phenyl, naphthyl, phenyl or naphthyl which is monosubstituted or disubstituted by C$_1$-C$_{12}$-alkyl, 2,4,6-trimethylphenyl, camphor-10-yl, a group of the formula —C(CH$_3$)$_2$—CH$_2$—NH—C(O)—CH=CH$_2$ or a group of the formula

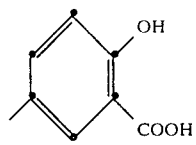

and B, provided that m=1, is a group of the formulae IV and V, and, if m=1 and if X is a group of the formula III, is, in addition, also a group of the formulae XI and XIV, and, if m=2, is a group of the formulae XVIII and XX, and, if m=2 and if X is a group of the formula III, is, in addition, also a group of the formula XXI, and, in the formulae IV, V, XI, XIV, XVIII, XX and XXI, R is hydrogen, $R^9$ is hydrogen, C$_1$-C$_6$-alkyl, allyl, benzyl, acetyl, acryloyl, 2-hydroxyethyl, cyanomethyl or oxyl, $R^{10}$ is hydrogen, methyl, phenyl or phenoxymethyl, $R^{11}$ is hydrogen, C$_1$-C$_4$-alkoxy, allyloxy, C$_1$-C$_{12}$-acyloxy, C$_1$-C$_{12}$-acylamino, C$_2$-C$_6$-alkoxycarbonyl or a group of the formula

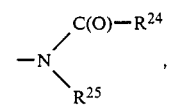

$R^{12}$ is hydrogen or C$_1$-C$_4$-alkyl, $R^{13}$ is hydrogen, $R^{14}$ is hydrogen, C$_1$-C$_{12}$-alkyl, allyl or benzyl, $R^{15}$ is hydrogen, methyl or benzyl, $R^{16}$ is hydrogen, methyl or ethyl, $R^{17}$ and $R^{18}$ are C$_1$-C$_4$-alkyl, $R^{19}$ and $R^{20}$ are hydrogen or C$_1$-C$_6$-alkyl, or, together, are C$_4$-C$_{11}$-alkylene, $R^{24}$ is C$_1$-C$_{12}$-alkyl, $R^{25}$ is hydrogen or C$_1$-C$_{12}$-alkyl and Z is a group of the formulae —OC(O)—R$^{29}$—C(O)O— or —N(R$^{30}$)—C(O)—R$^{31}$—C(O)—N(R$^3$))— in which $R^{29}$ is C$_2$-C$_{10}$-alkylene or o-, m- or p-phenylene, $R^{30}$ is hydrogen, C$_1$-C$_{12}$-alkyl or benzyl and $R^{31}$ is C$_2$-C$_{10}$-alkylene or o-, m-or p-phenylene, and acid addition salts thereof.

3. The composition according to claim 1 wherein m is the number 1 or 2, X is a direct bond or a group of the formula III in which $R^1$, $R^2$ and $R^3$ are hydrogen, A is methyl, ethyl, C$_{14}$-C$_{17}$-alkyl, methoxy, vinyl, amino, phenyl, p-methylphenyl, p-isopropylphenyl, p-dodecylphenyl, naphthyl, dinonylnaphthyl, camphor-10-yl, a group of the formula —C(CH$_3$)$_2$—CH$_2$—NH—C(O)—CH=CH$_2$ or a group of the formula

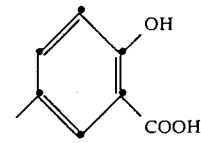

and B, provided that m=1, is a group of the formulae IV and V, and, if m=1 and if X is a group of the formula III, is, in addition, also a group of the formula XI and, if m=2, is a group of the formula XVIII and, if m=2 and if X is a group of the formula III, is, in addition, also a group of the formula XXI, and, in the formulae IV, V, XI, XVIII and XXI, R is hydrogen, $R^9$ is hydrogen, C$_1$-C$_6$-alkyl, allyl, benzyl, oxyl, acetyl, acryloyl, β-hydroxyethyl or cyanomethyl, $R^{10}$ is hydrogen, methyl or phenyl and $R^{11}$ is hydrogen or C$_1$-C$_4$-alkoxy, and acid addition salts thereof.

4. The composition according to claim 3 in which m is the number 1, B is a group of the formula IV, X is a direct bond or a group of the formula —O—CH$_2$—CH(OH)—CH$_2$— and A is as defined in claim 3.

5. The composition of claim 1 wherein said compound is of the formula

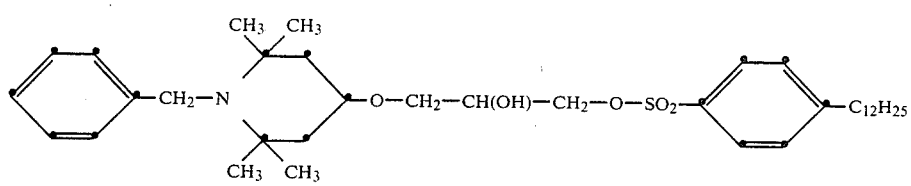
6. The composition of claim 1 wherein said compound is of the formula
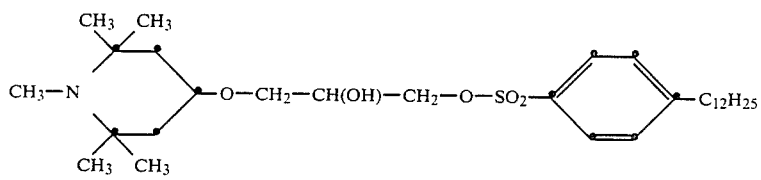
7. The composition of claim 1 wherein said compound is of the formula
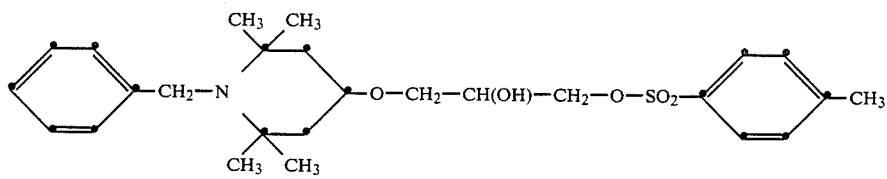
8. The composition of claim 1 wherein said compound is of the formula
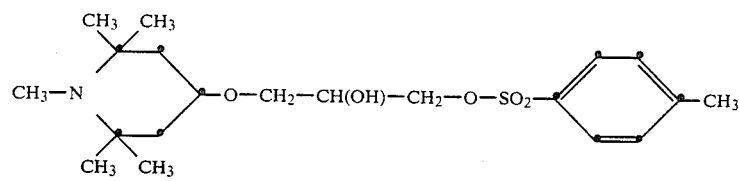
9. A composition of matter according to claim 1, wherein the acid-curable resin contains an acrylate component and is cured with completely etherified melamine resins.
* * * * *